United States Patent
Knudson et al.

(10) Patent No.: US 6,699,275 B1
(45) Date of Patent: Mar. 2, 2004

(54) STENT AND DELIVERY SYSTEM

(75) Inventors: Mark B. Knudson, Shoreview, MN (US); John P. Sopp, Forest Lake, MN (US); Timothy R. Conrad, Eden Prairie, MN (US)

(73) Assignee: EnteroMedics Inc., St. Paul, MN (US)

( * ) Notice: Subject to any disclaimer, the term of this patent is extended or adjusted under 35 U.S.C. 154(b) by 0 days.

(21) Appl. No.: 10/269,878

(22) Filed: Oct. 11, 2002

(51) Int. Cl.[7] ................................................. A61F 2/06
(52) U.S. Cl. ........................ 623/1.12; 604/27; 606/108
(58) Field of Search ............................... 623/1.11, 1.12, 623/1.15, 1.16, 1.17, 1.18, 1.19, 1.2, 1.21, 1.22, 1.42, 1.43; 606/108

(56) References Cited

U.S. PATENT DOCUMENTS

| | | | |
|---|---|---|---|
| 5,449,373 A | 9/1995 | Pinchasik et al. | 623/1.42 |
| 5,695,516 A | 12/1997 | Fischell et al. | 606/198 |
| 5,855,563 A * | 1/1999 | Kaplan et al. | 604/509 |
| 6,071,305 A * | 6/2000 | Brown et al. | 623/1.43 |
| 6,206,915 B1 | 3/2001 | Fagan et al. | 606/194 |
| 6,253,443 B1 * | 7/2001 | Johnson | 29/557 |
| 6,254,632 B1 * | 7/2001 | Wu et al. | 623/1.15 |
| 6,273,913 B1 | 8/2001 | Wright et al. | 623/1.42 |
| 6,287,291 B1 * | 9/2001 | Bigus et al. | 604/523 |
| 6,312,454 B1 * | 11/2001 | Stockel et al. | 623/1.11 |
| 6,558,733 B1 * | 5/2003 | Hossainy et al. | 427/2.24 |
| 6,562,065 B1 * | 5/2003 | Shanley | 623/1.15 |
| 6,569,145 B1 * | 5/2003 | Shmulewitz et al. | 604/509 |
| 6,579,305 B1 * | 6/2003 | Lashinski | 623/1.11 |

FOREIGN PATENT DOCUMENTS

JP         11347131      * 12/1999

* cited by examiner

Primary Examiner—Corrine McDermott
Assistant Examiner—Thomas J Sweet
(74) Attorney, Agent, or Firm—Merchant & Gould P.C.

(57) ABSTRACT

An intraluminal stent comprises a reticulated tube having an un-deployed diameter and expandable to an enlarged diameter. When the tube is at the un-deployed diameter, the tube has cell-defining portions with opposing surfaces defining an open cell bounded by the cell-defining portions.

8 Claims, 5 Drawing Sheets

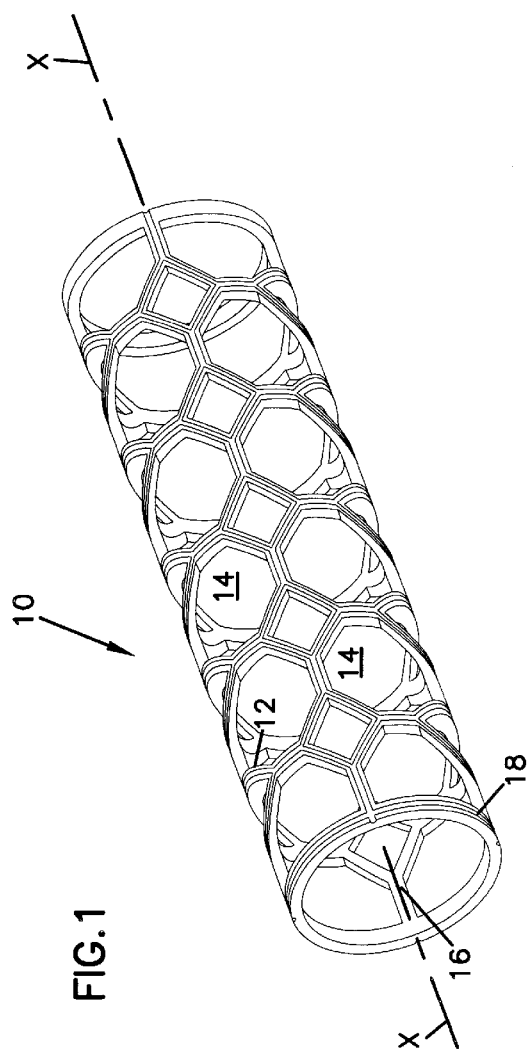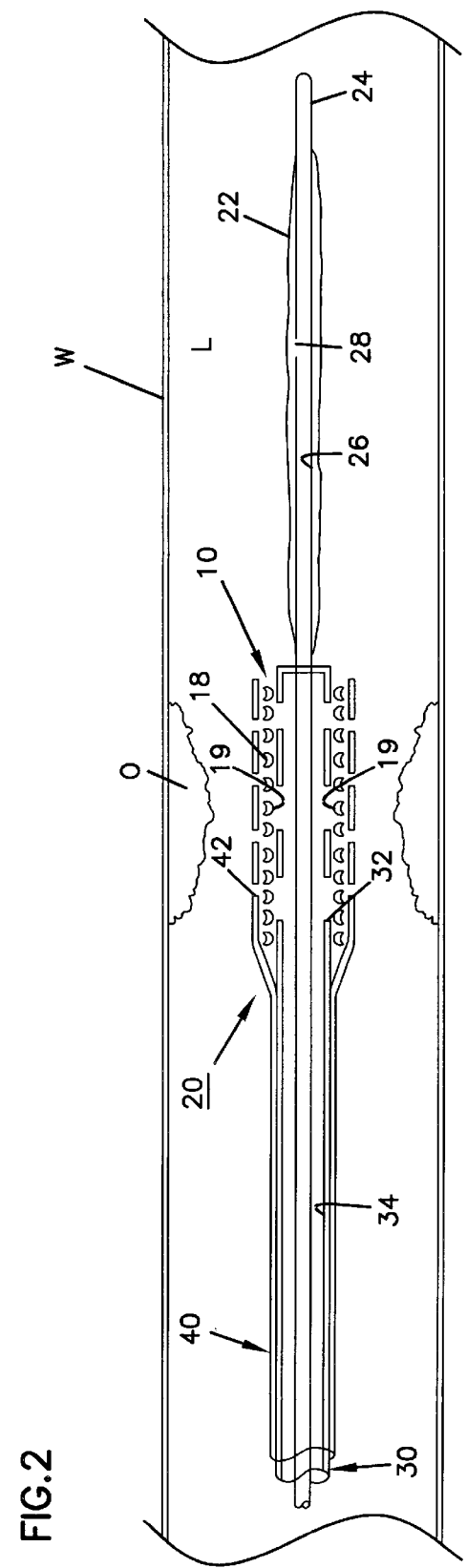
FIG.1
FIG.2

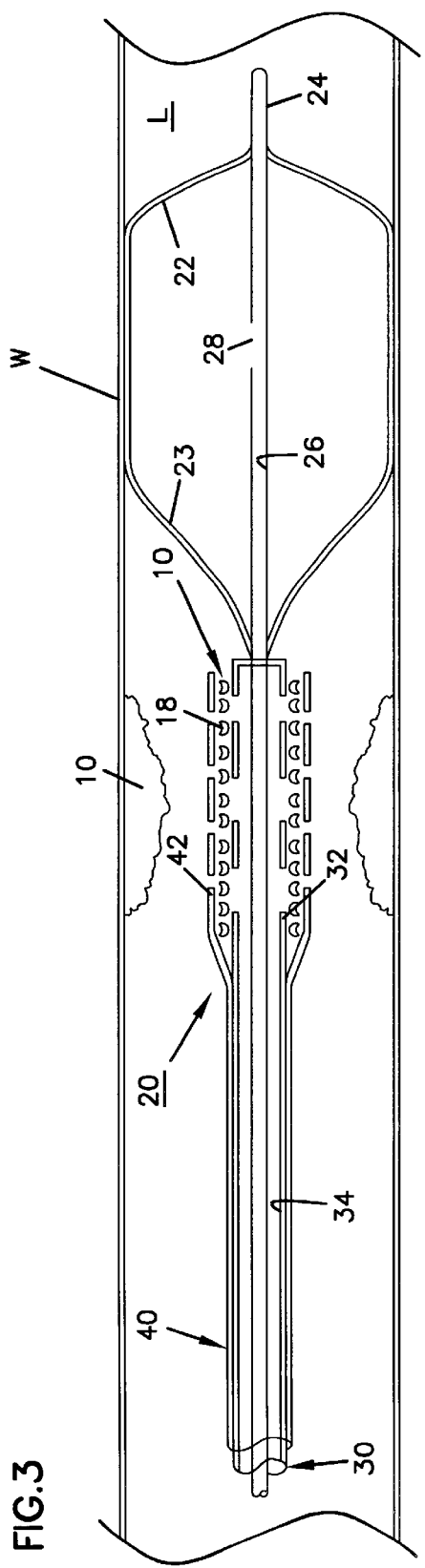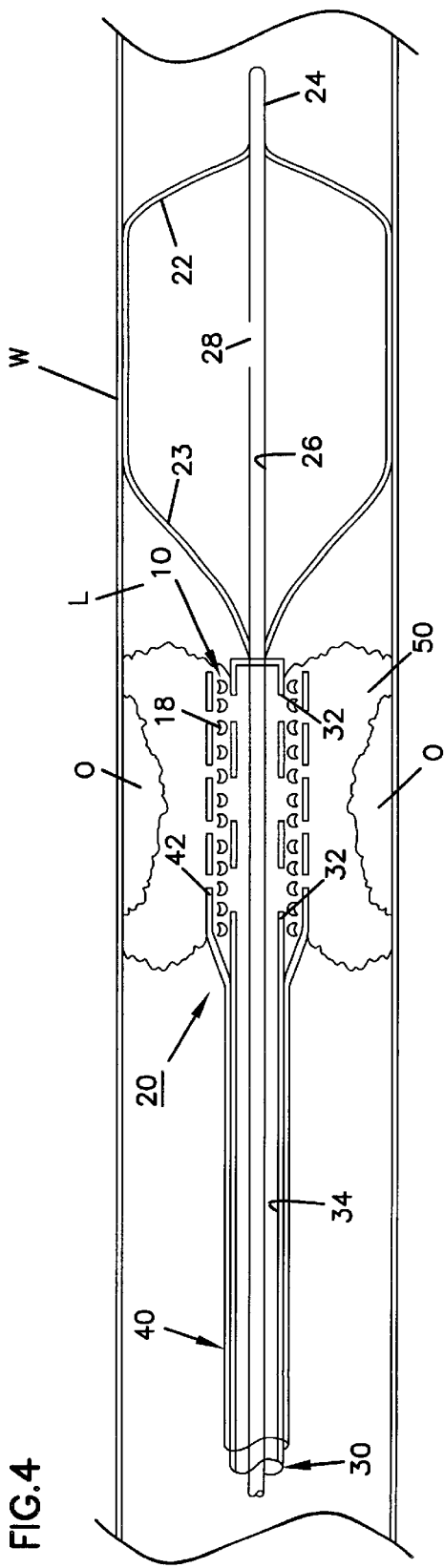

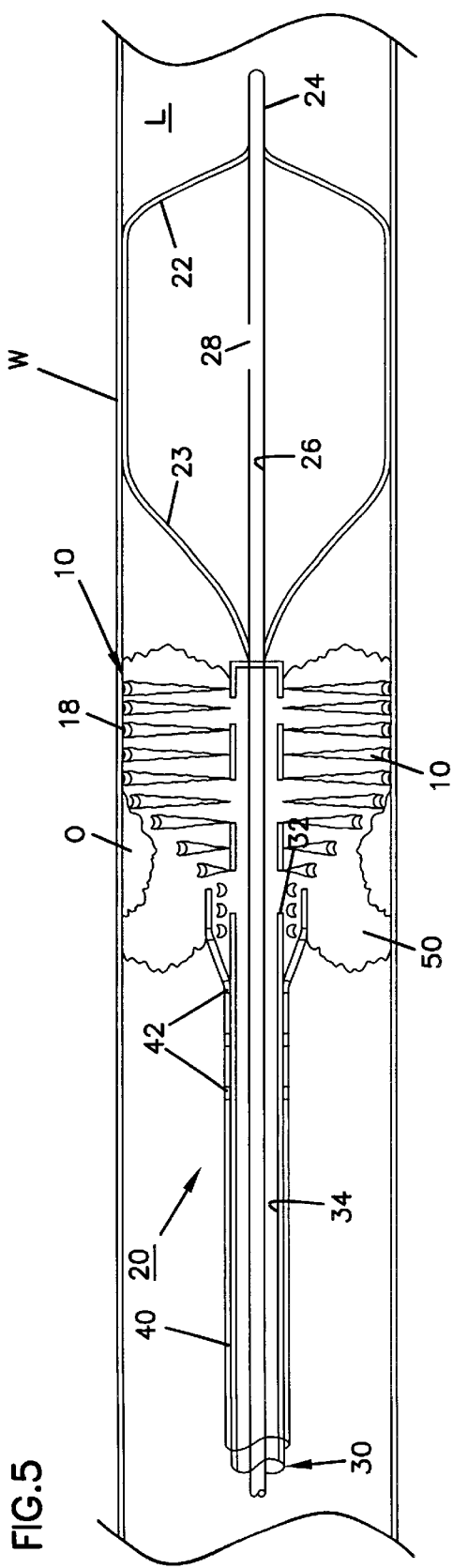
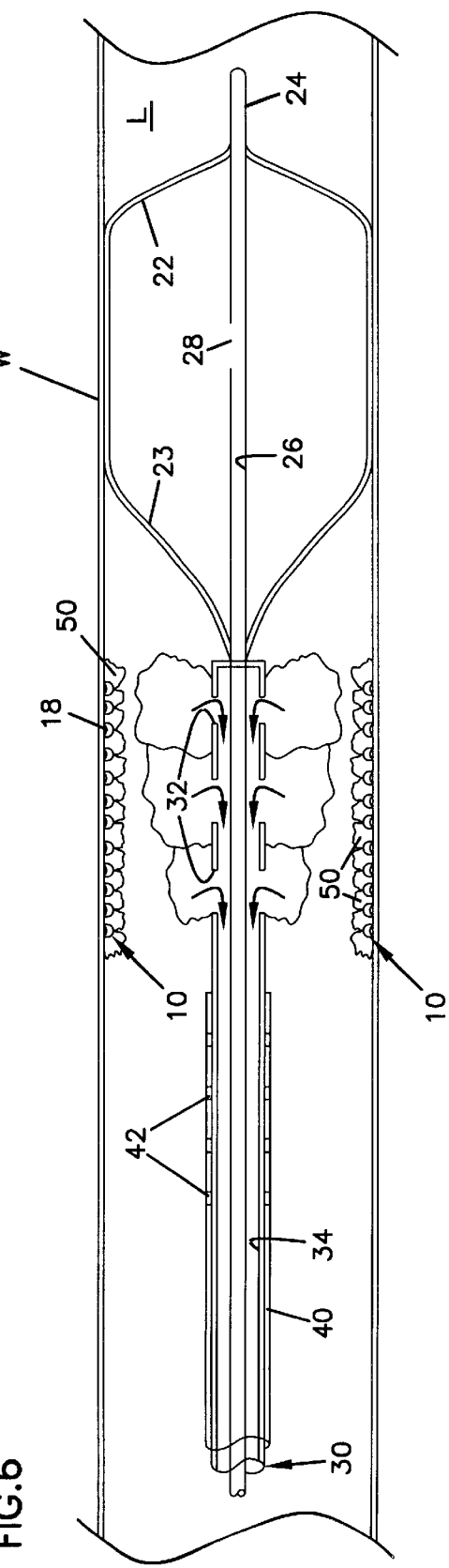

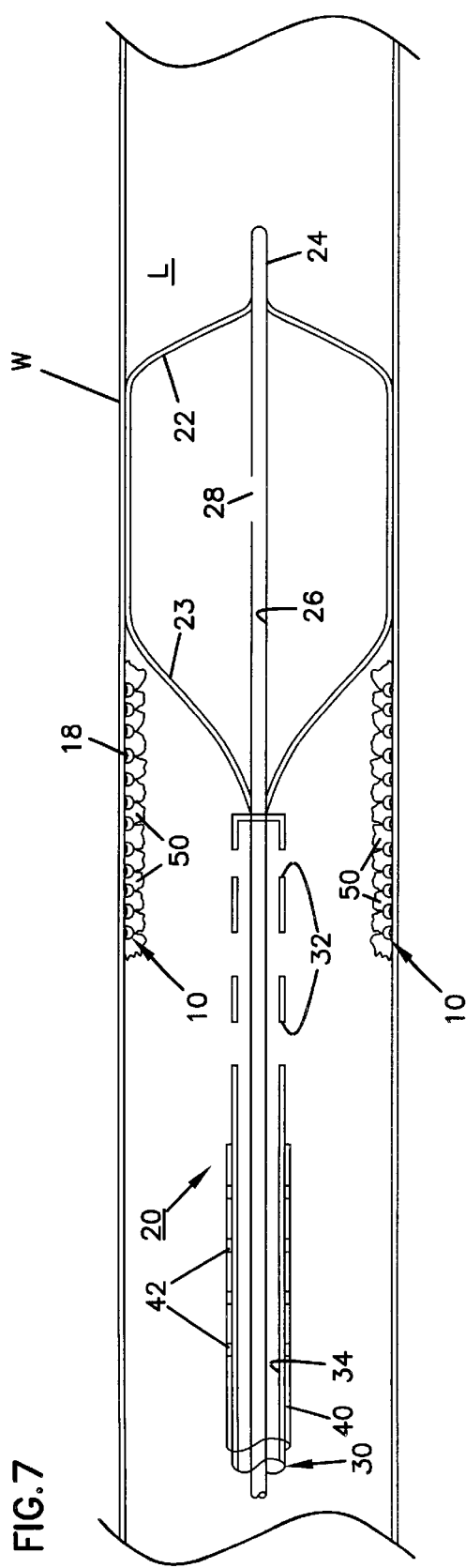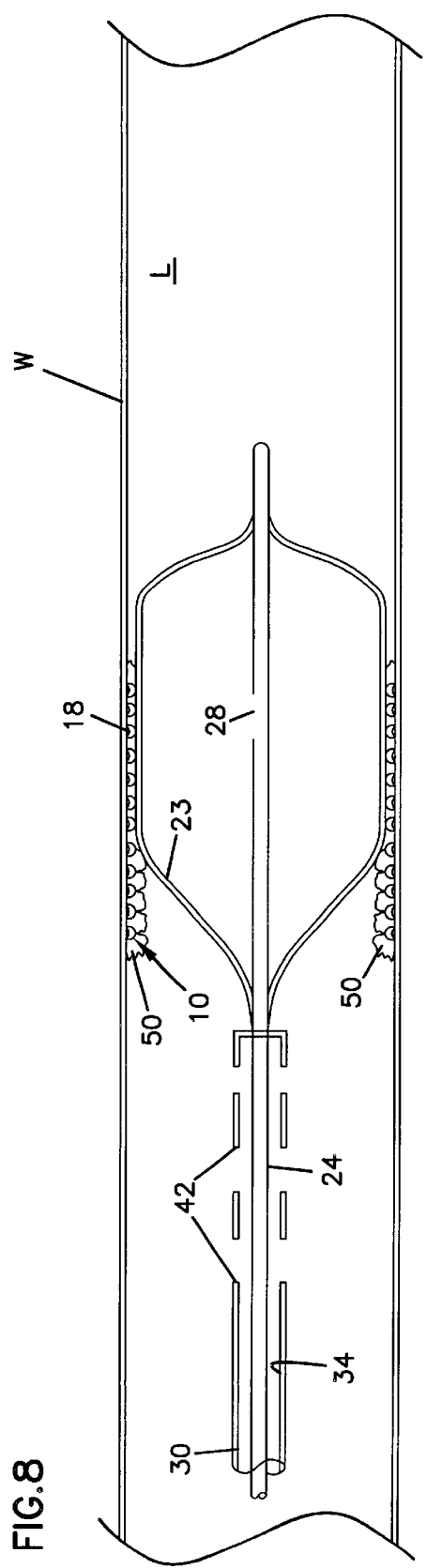

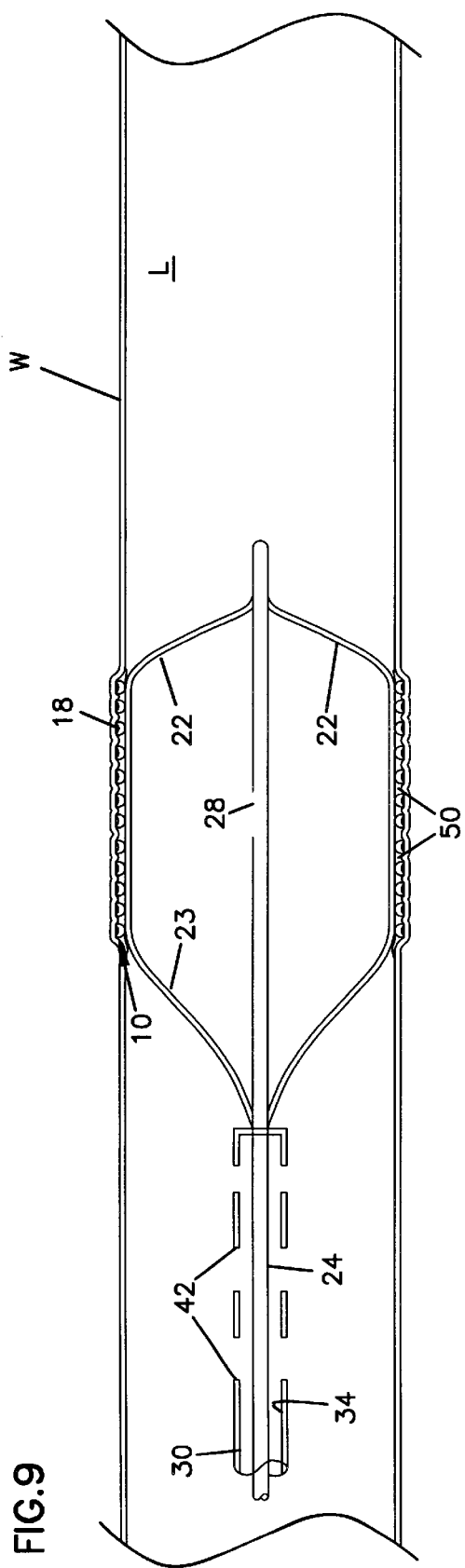
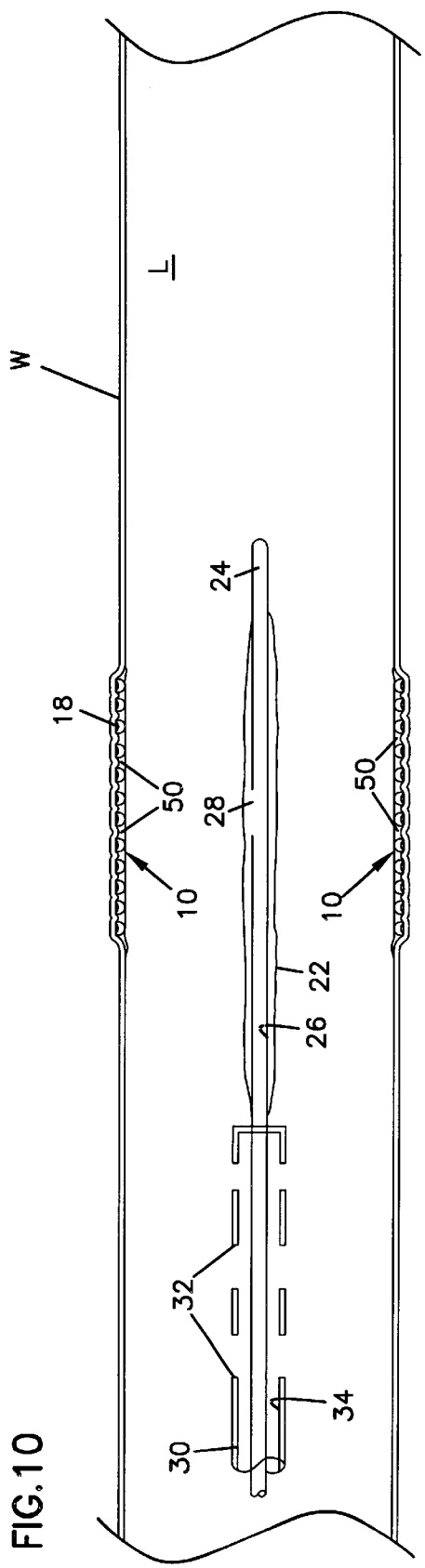
FIG.9
FIG.10

STENT AND DELIVERY SYSTEM

BACKGROUND OF THE INVENTION

1. Field of the Invention

This invention pertains to stents for use in intraluminal applications. More particularly, this invention pertains to a novel structure for such stents and a novel delivery tool and method.

2. Description of the Prior Art

Stents are widely used for numerous applications where the stent is placed in the lumen of a patient and expanded. Such stents may be used in coronary or other vasculature (such as carotid arteries or peripheral arteries), as well as other body lumens (e.g., biliary lumens).

Commonly, stents are cylindrical members. The stents expand from reduced diameters to enlarged diameters.

Stents may be self-expanding or may require the application of force to expand. Self-expanding stents are commonly formed of material which (when in the reduced diameter state) are biased to expand to the enlarged diameter. Such stents are carried on catheters with a sliding sheath placed over the stent and resisting the natural bias of the stent. At a desired delivery site, the sheath is retracted and the stent is free to expand to the enlarged diameter with an outer wall of the stent opposing and abutting an inner wall of the body lumen.

Non-self-expanding stents are commonly placed on a balloon catheter with the stent in the reduced-diameter state. So placed, the stent is advanced on the catheter to a placement site. At the site, the balloon is inflated to expand the stent to the enlarged diameter. The balloon is deflated and removed, leaving the enlarged diameter stent in place. So used, such stents are used to expand occluded sites within a patient's vasculature or other lumen.

Examples of prior art stents are numerous. For example, U.S. Pat. No. 5,449,373 to Pinchasik et al. teaches a stent with at least two rigid segments joined by a flexible connector. U.S. Pat. No. 5,695,516 to Fischell teaches a stent with a cell having a butterfly shape when the stent is in a reduced-diameter state. Upon expansion of the stent, the cell assumes a hexagonal shape.

More recently, significant attention has been paid to stents having drug coatings. Such drug-eluding stents have been developed to address a restenosis problem associated with stents. Restenosis is the tendency of an occlusion to reappear after having been treated by a stent. An example stent having drug storing and metering capabilities is disclosed in U.S. Pat. No. 6,206,915, which is hereby incorporated by reference in its entirety. It is hoped that restenosis rates would reduce following the introduction of drug-coated stents were the drug-coating is selected to inhibit restenosis.

While having a potential to being a significant improvement in stent design, drug-coated stents continue to have defects in application. For example, there are few choices of drugs and dosages in drug-coated stents. Also, current designs of drug-coated stents deplete the drug coating over a relatively short period of time (e.g., a few days).

SUMMARY

According to a preferred embodiment of the present invention, an intraluminal stent is disclosed comprising a reticulated tube having an un-deployed diameter and expandable to an enlarged diameter. When the tube is at the rest diameter, the tube has cell-defining portions with opposing surfaces defining an open cell bounded by the cell-defining portions.

BRIEF DESCRIPTION OF THE DRAWINGS

FIG. 1 is a perspective view of a stent according to the present invention;

FIG. 2 is a side sectional view of a delivery system according to present invention shown in a body lumen;

FIG. 3 is the view of FIG. 2 with a distal balloon shown in an inflated state;

FIG. 4 is the view of FIG. 3 following ejection of a drug-laden hydrogel into the body lumen and surrounding the occlusion;

FIG. 5 is the view of FIG. 4 showing partial expansion of the stent within the body lumen;

FIG. 6 is the view of FIG. 5 showing complete expansion of the stent within the body lumen and showing removal of excess amounts of hydrogel from the body lumen;

FIG. 7 is the view of FIG. 6 following completion of removal of the excess amounts of hydrogel and showing initiation of a compression of the stent and remaining hydrogel by the distal balloon;

FIG. 8 is the view of FIG. 7 showing partial compression of the stent and hydrogel by the balloon;

FIG. 9 is the view of FIG. 8 showing complete expansion of the stent and compression of the hydrogel by the distal balloon;

FIG. 10 is the view of FIG. 9 showing the balloon and in deflated state with the delivery system less the stent in process of removal from the body lumen.

DESCRIPTION OF THE PREFERRED EMBODIMENT

Referring now to the several drawing figures in which identical elements are numbered identically, a description of the preferred embodiment of the present invention will now be provided. Where several embodiments are shown, common elements are similarly numbered and not separately described with the addition of apostrophes to distinguish the embodiments.

A stent 10 is schematically shown in FIG. 1. The stent 10 is a reticulated tube having a plurality of struts 12, which operate as cell-defining portions to define a plurality of open cells 14 extending through an outer cylindrical wall of the stent 10.

The struts 12 have an inner surface 16 opposing a longitudinal stent axis X-X. An outer surface of the cell-defining portions is provided with a surface depression 18 in the form of a groove. The groove is concave in shape and extends along the outer surface of the cell-defining portions. As a result, each of the struts 12, in cross-section, presents a concave groove on an outer surface of the strut 12. The groove is disposed such that when the stent is urged against the wall W of a body lumen L, the groove becomes an enclosed chamber captured between the struts 12 and the wall W of the body lumen L as will be more described. In one embodiment the depressions 18 cover or coincide with at least 10% of a total outer surface area of the struts. In another embodiment, the depressions 18 coincide with at least 25% or at least 50% of the total area defined by the outer surfaces of the struts 12. As best shown in FIG. 2, inner surfaces 19 of the struts are preferably rounded so as to have a convex curvature.

In FIG. 1, the stent 10 is shown in an enlarged or expanded diameter. The material of the stent 10 defines the plurality of cells 14. The cells 14 are bounded areas which are open (i.e., extend through the wall thickness of the stent 10).

The stent may be formed through any suitable means including laser or chemical milling. In such processes, a hollow cylindrical tube is milled to remove material and form the open cells 14. By way of non-limiting the example, the width and thickness of the stent 10 is sized for a particular application. For example, for placement in artery, the stent 10 may be sized such that is enlarged diameter is only slightly greater than the internal diameter of the artery. For example, for a 5 mm diameter artery, the stent may have an expanded diameter of about 5.5 mm and a reduced diameter of about 2 mm such that the stent may be placed on a catheter and advanced through the arterial system to a deployment site as is conventional.

The specific structure and geometry of the stent 10 as shown in FIG. 1 is for illustration purposes only. There are numerous geometries and shapes of stents and cell-defining portions of stents in the prior art which can be applicable to the present invention. Also, the stent may be lined with an inner or outer sleeve such as polyester fabric or EPTFE for tissue ingrowth. The stent may be coated with radiopaque coatings such as platinum, gold, tungsten, or tantalum. The stent may be formed of any one of a wide variety of previously known materials including, without limitation, stainless steel, nitinol, MP35N, tantalum, platinum, gold, Elgiloy and Phynox.

In the embodiments shown and described in the present application, the stent 10 is shown as a self-expanding stent preferably formed of nitinol. However, the stent 10 may be a non-self-expanding stent of the construction requiring the application of force (such as inflation of a balloon) to expand the stent to the expanded diameter as is known in the prior art.

FIG. 2 shows a delivery system 20 according to the present invention in position within a body lumen L defined by a wall W. In a preferred embodiment, the wall W may be an artery such as a coronary artery. Also shown in FIG. 2, an obstruction O (such as arterial plaque or thrombus) is located within the lumen L and at least partially occluding the lumen L.

The delivery system 20 includes a distal balloon 22 which may be carried on the distal tip of a catheter or, as shown, on the distal tip of a guide wire 24 where the guide wire contains a hollow lumen 26 and with an opening 28 in communication with the balloon 22. Accordingly, fluid may be selectively admitted under pressure through the lumen 26 and through the opening 28 to cause inflation of the balloon 22. In FIG. 2, the balloon 22 is shown in a deflated state for unobstructed advancement through the lumen L.

A catheter 30 is positioned coaxially surrounding the guide wire 24 and terminating on a proximal side of the balloon 22. At a distal end of the catheter 30, the outer cylindrical wall of the catheter 30 is provided with a plurality of openings 32 in communication with an inner hollow lumen 34 of the catheter 30 such that material may be ejected from the lumen 34 and through the openings 32 as will be described.

The stent 10 is positioned surrounding the distal end of the catheter 30 with the stent 10 in a reduced diameter or compressed state. An outer sheath 40 surrounds the catheter 30 and the stent 10. At a distal end, the sheath 40 is provided with a plurality of openings 42 positioned opposing the stent 10. As a result, there is fluid flow communication between the lumen 34, openings 32, 42 and through the interstitial space between the struts 12 of the stent 10 such that material may be passed between the exterior of the sheath 40 and the catheter lumen 34 as will become apparent.

The stent 10 is a self-expanding stent. When the sheath 40 is retracted proximally, the sheath 40 exposes the stent 10 which may now expand under its bias to an expanded diameter.

In use, the delivery system 20 as described is advanced to the position shown in FIG. 2 with the balloon 22 in a deflated state and position distally to the obstruction O. The stent 10 is positioned within the obstruction O. Preferably, the stent 10 has an axial length greater than an axial length of the obstruction O.

With the delivery system 20 positioned as described with respect to FIG. 2, the balloon 22 is inflated as illustrated in FIG. 3. When inflated, the balloon 22 is urged against the wall W of the vessel. The balloon 22 is shown with a proximal end 23 having a sloped shape at an angle of approximately 45 degrees to the guide wire 24 such that the end 23 is generally conical in shape.

With the balloon inflated in shown in FIG. 3, fluid flow (e.g., arterial blood flow) distally past the obstruction O is prevented. If desired, a proximal balloon (not shown) could be inflated on a proximal side of the stent 10 to isolate the obstruction O between two balloons. An additional lumen (not shown) could be formed within the guide wire 24 or in an additional catheter to permit blood flow to flow from a proximal side of the second balloon (not shown) to the distal side of the balloon 22 thereby maintaining blood flow distal to balloon 22.

With the balloon 22 inflated as shown in FIG. 3, a hydrogel 50 is ejected through the lumen 34 and through the openings 32, 42 to set up surrounding the obstruction O as illustrated in FIG. 4. The hydrogel 50 is preferably drug-laden with a therapeutic amount of a drug to prevent restonosis or otherwise provide desired therapy to the artery wall W. Examples of such drugs carried within the hydrogel 50 may include heparin, heparin fragments, angiotensin converting enzyme inhibitors, angiopeptin, cyclosporin and antibiotics such as rapamycin. Other suitable drugs are disclosed in U.S. Pat. No. 6,273,913, which is hereby incorporated by reference in its entirety.

As shown in FIG. 4, the hydrogel 50 completely surrounds the occlusion O. After the hydrogel 50 has been ejected and set as shown in FIG. 4, the sheath 40 is retracted proximally such that the stent 10 may begin to expand as illustrated in FIG. 5.

Complete retraction of the sheath 40 results in complete expansion of the stent 10 as illustrated in FIG. 6 with the stent 10 abutting the wall W of the vessel. As the stent 10 expands through the hydrogel 50, the stent 10 fractures the hydrogel material.

Application of a vacuum to the lumen 34 draws the fractured hydrogel into the catheter lumen 34 and out of the vessel lumen L as illustrated in FIG. 6. This results in only a small portion of the hydrogel 50 remaining surrounding the stent 10.

As the stent 10 is urged against the wall W of the vessel, opposing surfaces of the wall W and the concave cell-defining surfaces 18 (i.e., grooves) define a chamber captured between the stent 10 and the wall W. A portion of the drug-laden hydrogel 50 is captured within the chamber and abutting the wall W. At this point, the balloon 22 and remaining portions of the delivery system 20 are retracted as illustrated in FIGS. 7–9 with the balloon 22 urging further expansion of the stent 10 and urging the hydrogel 50 to be compressed within the interstitial spaces of the stent 10. Following this further expansion, the balloon 22 maybe deflated as illustrated in FIG. 10 such that the remaining elements of the delivery system (i.e., the complete delivery system 20 less the stent 10) can be proximally withdrawn through the vessel lumen L.

The above description of apparatus and method results in the stent 10 being positioned urging the obstruction O against the wall W of the vessel and maintaining the wall W of the vessel in an expanded and open state. A portion of the drug-laden hydrogel 50 is captured within the chamber defined between the concave surfaces 18 of the stent 10 and the wall W of the vessel. Therefore, the drug may be eluded through the hydrogel 50 over time to provide a therapeutic effect to the wall W of the vessel. Also, a portion of the hydrogel 50 may reside within the interstitial spaces or open cells between opposing cell-defining struts 12 to provide additional therapeutic effect.

From the foregoing, the present invention has been shown in a preferred embodiment. Modifications and equivalents are intended to be included within the scope of the appended claims.

What is claimed is:

1. A stent delivery system comprising:

a catheter having an inner lumen;

a stent carried on said catheter;

a sheath surrounding said catheter and surrounding said stent in said reduced diameter state, said sheath proximally retractable on said catheter to expose said stent and permit said stent to expand to an expanded state; and a plurality of openings formed through both of said sheath and said catheter to permit flow of material between an exterior of said sheath and said catheter inner lumen.

2. A delivery system according to claim 1 wherein the stent includes an outer surface including a plurality of surface depressions disposed to define one or more chambers which may be disposed between said outer surface and a vessel wall when said stent is deployed.

3. A delivery system according to claim 2 further comprising a drug disposed in said chamber.

4. A delivery system according to claim 3 wherein said drug within said chamber is carried in a medium.

5. A delivery system according to claim 4 wherein said medium is selected to deliver said drug over an extended period of time.

6. A delivery system according to claim 5 wherein said medium is a hydrogel.

7. A delivery system according to claim 2 wherein said plurality of surface depressions are formed by one or more grooves disposed in said outer surface.

8. A delivery system according to claim 7 wherein the one ore more grooves comprise concave grooves formed in said outer surface.

* * * * *

UNITED STATES PATENT AND TRADEMARK OFFICE
CERTIFICATE OF CORRECTION

PATENT NO.     : 6,699,275 B1
DATED          : March 2, 2004
INVENTOR(S)    : Knudson et al.

It is certified that error appears in the above-identified patent and that said Letters Patent is hereby corrected as shown below:

Column 5,
Line 29, "stent in a reduced" should read -- stent in said reduced --.

Signed and Sealed this

Eighth Day of June, 2004

JON W. DUDAS
*Acting Director of the United States Patent and Trademark Office*